US005834470A

United States Patent [19]
Maurer

[11] Patent Number: 5,834,470
[45] Date of Patent: Nov. 10, 1998

[54] 6-(2-IMIDAZOLINYLAMINO) QUINOXALINE COMPOUNDS USEFUL AS α-2 ADRENORECEPTOR AGONISTS

[75] Inventor: Peter Julian Maurer, Cincinnati, Ohio

[73] Assignee: The Procter & Gamble Company, Cincinnati, Ohio

[21] Appl. No.: 911,570

[22] Filed: Aug. 14, 1997

Related U.S. Application Data

[63] Continuation of Ser. No. 169,785, Dec. 17, 1993, abandoned.

[51] Int. Cl.$^6$ ..................................................... A61K 31/50
[52] U.S. Cl. ............................................................ 514/249
[58] Field of Search ............................................. 514/249

[56] References Cited

U.S. PATENT DOCUMENTS

| | | | |
|---|---|---|---|
| 3,890,319 | 6/1975 | Danielewicz et al. | 260/250 |
| 4,029,792 | 6/1977 | Danielewicz et al. | 424/251 |
| 4,036,976 | 7/1977 | Neumann | 424/273 |
| 4,217,356 | 8/1980 | Neumann | 424/270 |
| 4,398,028 | 8/1983 | Neumann | 544/331 |
| 5,021,416 | 6/1991 | Gluchowski | 514/249 |
| 5,091,528 | 2/1992 | Gluchowski . | |
| 5,180,721 | 1/1993 | Burke | 514/213 |
| 5,231,096 | 7/1993 | Gluchowski et al. | 514/249 |
| 5,281,591 | 1/1994 | Burke | 514/213 |

FOREIGN PATENT DOCUMENTS

| | | | |
|---|---|---|---|
| 0 047 328 | 3/1982 | European Pat. Off. | C07D 403/12 |
| 0 025 269 | 3/1991 | European Pat. Off. | A61K 31/155 |
| 2 638 356 | 4/1990 | France | A61K 31/415 |

OTHER PUBLICATIONS

Cambridge D., "UK–14,304, A Potent and Selective α$_2$–Agonist for the Characterisation of α–Adrenoceptor Subtypes", *European Journal of Pharmacology*, vol. 72 (1981), pp. 413–415.

Chapleo, C. B., J. C. Doxey, P. L. Myers, M. Myers, C. F. C. Smith and M. R. Stillings, "Effect of 1,4–Dioxanyl Substitution on the Adrenergic Activity of Some Standard α–Adrenoreceptor Agents", *European Journal of Medicinal Chemistry*, vol. 24 (1989), pp. 619–622.

Chapleo, C. B., R. C. M. Butler, D. C. England, P. L. Myers, A. G. Roach, C. F. C. Smith, M. R. Stillings and I. F. Tulloch, "Heteroaromatic Analogues of the α$_2$–Adrenoreceptor Partial Agonist Clondine", *J. Med. Chem.*, vol. 32 (1989), pp. 1627–1630.

Clare, K. A., M. C. Scrutton and N.T. Thompson, "Effects of α–adrenoceptor agaonists and of related compounds on aggregation of, and on adenylate cyclose activity in, human platelets", *Br. J. Pharmac.*, vol. 82 (1984), pp. 467–476.

Timmermans, P. B. M. W. M. and P. A. van Zwieten, "α–Adrenoceptor Agonists and Antagonists", *Drugs of the Future*, vol. 9, No. 1 (Jan., 1984), pp. 41–55.

Timmermans, P. B. M. W. M., A. T. Chiu and M. J. M. C. Thoolen, "12.1 α–Adrenergic Receptors", *Comprehensive Medicinal Chemistry*, vol. 3, Membranes & Receptors (1990), pp. 133–185.

Timmermans, P. B. M. W. M., A. de Jonge, M. J. M. C. Thoolen, B. Wilffert, H. Batnik and P. A. van Zwieten, "Quantitative Relationships between α–Adrenergic Activity and Binding Affinity of αAdrenoceptor Agonists and Antagonists", *J. Med. Chem.*, vol. 27 (1984), pp. 495–503.

Megens, A. A. H. P., J. E. Leysen, F. H. L. Awouters and C. J. E. Niemegeers, "Further Validation of In Vivo and In Vitro Pharmacological Procedures for Assessing the α$_2$/α$_1$–Selectivity of Test Compounds: (2) α–Adrenoceptor Agonists", *European Journal of Pharmacology*, vol. 129 (1986), pp. 57–64.

van Meel, J. C. A., A. de Jonge, P. B. M. W. M. Timmermans and P. A. van Zwieten, "Selectivity of Some *Alpha* Adrenoceptor Agonists for Peripheral *Alpha*–1 and *Alpha*–2 Adrenoceptors in the Normotensive Rat", *The Journal of Pharmacology and Experimental Therapeutics*, vol. 219, No. 3 (1981), pp. 760–767.

Zinchenko, T. M., "Investigation of Autoallergenic Action of Dibutyl and Dioctyl Phthalates", *Gig. Sanit.*, vol. 1, pp. 79–80 (1981).

*Primary Examiner*—Zohreh Fay
*Attorney, Agent, or Firm*—Richard A. Hake; Mary Pat McMahon; Milton B. Graff, IV

[57] ABSTRACT

The subject invention involves methods of treating nasal congestion comprising administration, to a human or lower animal in need of such treatment of a safe and effective amount of a compound having the following structure:

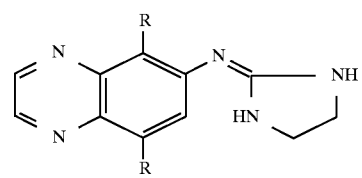

wherein
(a) R is unsubstituted C$_1$–C$_3$ alkanyl or alkenyl; and
(b) R' is selected from hydrogen; unsubstituted C$_1$–C$_3$ alkanyl or alkenyl, unsubstituted C$_1$–C$_3$ alkylthio or alkoxy; hydroxy; thiol; and halo.

The subject invention also involves the use of such compounds for preventing or treating other respiratory, ocular and/or gastrointestinal disorders.

10 Claims, No Drawings

6-(2-IMIDAZOLINYLAMINO) QUINOXALINE COMPOUNDS USEFUL AS α-2 ADRENORECEPTOR AGONISTS

This is a continuation of application Ser. No. 08/169,785 filed on Dec. 17, 1993 now abandoned.

TECHNICAL FIELD

The subject invention relates to certain substituted 6-(2-imidazolinylamino)quinoxaline compounds. The compounds have been found to be selective alpha-2 adrenoceptor agonists and are useful for treatment of one or more of respiratory disorders, particularly nasal congestion; ocular disorders, particularly glaucoma; and gastrointestinal disorders, particularly diarrhea.

BACKGROUND OF THE INVENTION

Information regarding alpha adrenergic receptors, agonists and antagonists, in general, and regarding compounds related in structure to those of the subject invention are disclosed in the following references: Timmermans, P.B.M.W.M., A. T. Chiu & M.J.M.C. Thoolen, "12.1 α-Adrenergic Receptors", *Comprehensive Medicinal Chemistry,* Vol. 3, Membranes & Receptors, P. G. Sammes & J. B. Taylor, eds., Pergamon Press (1990), pp. 133–185; Timmermans, P.B.M.W.M. & P. A. van Zwieten, "α-Adrenoceptor Agonists and Antagonists", *Drugs of the Future,* Vol. 9, No. 1, (January, 1984), pp. 41–55; Megens, A.A.H.P., J. E. Leysen, F.H.L. Awouters & C.J.E. Niemegeers, "Further Validation of in vivo and in vitro Pharmacological Procedures for Assessing the $\alpha_1$ and $\alpha_2$-Selectivity of Test Compounds: (2) α-Adrenoceptor Agonists", *European Journal of Pharmacology,* Vol. 129 (1986), pp. 57–64; Timmermans, P.B.M.W.M., A. de Jonge, M.J.M.C. Thoolen, B. Wilffert, H. Batink & P. A. van Zwieten, "Quantitative Relationships between α-Adrenergic Activity and Binding Affinity of α-Adrenoceptor Agonists and Antagonists", *Journal of Medicinal Chemistry,* Vol. 27 (1984) pp. 495–503; van Meel, J.C.A., A. de Jonge, P.B.M.W.M. Timmermans & P. A. van Zwieten, "Selectivity of Some Alpha Adrenoceptor Agonists for Peripheral Alpha-1 and Alpha-2 Adrenoceptors in the Normotensive Rat", *The Journal of Pharmacology and Experimental Therapeutics,* Vol. 219, No. 3 (1981), pp. 760–767; Chapleo, C. B., J. C. Doxey, P. L. Myers, M. Myers, C.F.C. Smith & M. R. Stillings, "Effect of 1,4-Dioxanyl Substitution on the Adrenergic Activity of Some Standard α-Adrenoceptor Agents", *European Journal of Medicinal Chemistry,* Vol. 24 (1989), pp. 619–622; Chapleo, C.B., R.C.M. Butler, D. C. England, P. L. Myers, A. G. Roach, C.F.C. Smith, M. R. Stillings & I. F. Tulloch, "Heteroaromatic Analogues of the $\alpha_2$-Adrenoceptor Partial Agonist Clondine", *J. Med. Chem.,* Vol. 32 (1989), pp. 1627–1630; Clare, K. A., M. C. Scrutton & N. T. Thompson, "Effects of ($\alpha_2$-Adrenoceptor Agonists and of Related Compounds on Aggregation of, and on Adenylate Cyclase Activity in, Human Platelets", *Br. J. Pharmac.,* Vol. 82 (1984), pp. 467–476; U.S. Pat. No. 3,890,319 issued to Danielewicz, Snarey & Thomas on Jun. 17, 1975; and U.S. Pat. No. 5,091,528 issued to Gluchowski on Feb. 25, 1992. However, many compounds related in structure to those of the subject invention do not provide the activity and specificity desirable when treating respiratory, ocular or gastrointestinal disorders.

It is particularly relevant to the subject invention that compounds found to be effective nasal decongestants are frequently found to have undesirable side effects, such as causing hypertension and insomnia. There is a need for new drugs which provide relief from nasal congestion without causing these undesirable side effects.

It is an object of the subject invention to provide novel compounds having substantial activity in preventing or treating nasal congestion.

It is a further object of the subject invention to provide such compounds which do not cause hypotension, drowsiness, hypertension, insomnia or other undesirable side effects.

It is also an object of the subject invention to provide novel compounds for treating cough, chronic obstructive pulmonary disease (COPD) and/or asthma.

It is also an object of the subject invention to provide novel compounds for treating glaucoma and/or diarrhea.

It is a still further object of the subject invention to provide such compounds which have good activity from peroral and/or topical dosing.

SUMMARY OF THE INVENTION

The subject invention relates to methods of treating nasal congestion comprising administration, to a human or lower animal in need of such treatment of a safe and effective amount of a compound having the following structure:

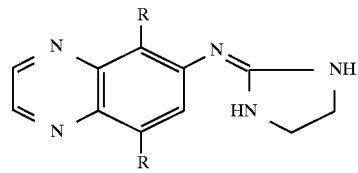

wherein:

(a) R is unsubstituted $C_1$–$C_3$ alkanyl or alkenyl; and (b) R' is selected from hydrogen; unsubstituted $C_1$–$C_3$ alkanyl or alkenyl; unsubstituted $C_1$–$C_3$ alkylthio or alkoxy; hydroxy; thiol; and halo.

The subject invention also relates to the use of such compounds for preventing or treating other respiratory, ocular and/or gastrointestinal disorders.

DETAILED DESCRIPTION OF THE INVENTION

As used herein, "alkanyl" means a saturated hydrocarbon substituent, straight or branched chain, unsubstituted or substituted.

As used herein, "alkenyl" means a hydrocarbon substituent with one double bond, straight or branched chain, unsubstituted or substituted.

As used herein, "alkylthio" means a substituent having the structure Q—S—, where Q is alkanyl or alkenyl.

As used herein, "alkoxy" means a substituent having the structure Q—O—, where Q is alkanyl or alkenyl.

The subject invention involves compounds having the following structures:

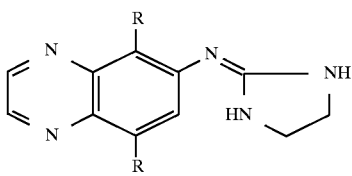

In the above structure, R is unsubstituted alkanyl or alkenyl having from 1 to about 3 carbon atoms. R is preferably alkanyl. R is more preferably methyl or ethyl, most preferably methyl.

In the above structure, R' is selected from hydrogen; unsubstituted alkanyl or alkenyl having from 1 to about 3 carbon atoms; unsubstituted alkylthio or alkoxy having from 1 to about 3 carbon atoms; hydroxy; thiol; and halo. R' is preferably hydrogen. R' is also preferably alkanyl, more preferably methyl or ethyl, most preferably methyl. R' which is alkylthio or alkoxy is preferably saturated, also preferably $C_1$ or $C_2$, more preferably methylthio or methoxy. R' which is halo is preferably chloro or bromo, more preferably chloro.

Preferred compounds of the subject invention are compounds having the following structure:

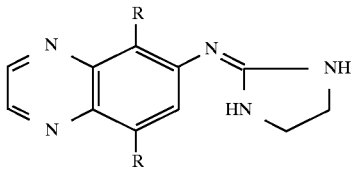

where R and R' are as indicated in the following table:

| Compound No. | R | R' |
| --- | --- | --- |
| 1 | $CH_3$ | H |

The compounds of the subject invention are particularly useful for the treatment of nasal congestion associated with allergies, colds, and other nasal disorders with associated nasal congestion, as well as their sequelae (for example, sinusitis and otitis). At the same time, it has been found that undesired side effects, such as hypotension, drowsiness, hypertension, or insomnia can be avoided. While not limited to a particular mechanism of action, the subject compounds are believed to provide advantages in the treatment of nasal decongestion over related compounds through their ability to interact with alpha-2 adrenoceptors. The subject compounds have been found to be alpha-2 adrenoceptor agonists which cause constriction of peripheral vascular beds in the turbinates. The subject compounds have been found to have only weak alpha-1 agonist activity, and have little or no effect on the central nervous system.

The compounds of the subject invention are also useful for the treatment of ocular disorders associated with increased intraocular pressure, such as glaucoma. The compounds are administered either perorally, or topically as drops, gels or creams directly to the surface of the mammalian eye.

The compounds of the subject invention are also useful for controlling gastrointestinal motility disorders, such as diarrhea, by antimotility and antisecretory actions on the gastrointestinal tract.

The pharmacological activity and selectivity of the subject compounds can be determined using published test procedures. The alpha-2 selectivity of the compounds is determined by measuring receptor binding affinities and in vitro functional potencies in a variety of tissues known to possess alpha-2 and/or alpha-1 receptors. (See, e.g., *The Alpha-2 Adreneraic Receptors,* L. E. Limbird, ed., Humana Press, Clifton, N.J.) The following in vivo assays are typically conducted in rodents or other species. Central nervous system activity is determined by measuring locomotor activity as an index of sedation. (See, e.g., Spyraki, C. & H. Fibiger, "Clonidine-induced Sedation in Rats: Evidence for Mediation by Postsynaptic Alpha-2 Adrenoreceptors", *J. Neural. Trans.,* Vol. 54 (1982), pp. 153–163). Nasal decongestant activity is measured using rhinomanometry as an estimate of nasal airway resistance. (See, e.g., Salem, S. & E. Clemente, "A New Experimental Method for Evaluating Drugs in the Nasal Cavity", *Arch. Otolarynng,* Vol. 96 (1972), pp. 524–529). Antiglaucoma activity is determined by measuring intraocular pressure. (See, e.g., Potter, D., "Adrenergic Pharmacology of Aqueous Human Dynamics", *Pharmacol. Rev.,* Vol. 13 (1981), pp. 133–153). Antidiarrheal activity is determined by measuring the ability of the compounds to inhibit prostaglandin-induced diarrhea. (See, e.g., Thollander, M., P. Hellstrom & T. Svensson, "Suppression of Castor Oil-induced Diarrhea by Alpha-2 Adrenoceptor Agonists", *Aliment. Pharmacol. Therap.,* Vol. 5 (1991), pp. 255–262). Antiasthma activity is determined by measuring the effect of the compound on bronchoconstriction associated with pulmonary challenges such as inhaled antigens. (See, e.g., Chang, J. J. Musser & J. Hind, "Effects of a Novel Leukotriene $D_4$ Antagonist with 5-Lipoxygenase and Cyclooxygenase Inhibitory Activity, Wy-45,911, on Leukotriene-$D_4$-and Antigen-Induced Bronchoconstriction in Guinea Pig", *Int. Arch. Allergy Appl. Immun.,* Vol. 86 (1988), pp. 48–54; and Delehunt, J., A. Perruchound, L. Yerger, B. Marchette, J. Stevenson & W. Abraham, "The Role of Slow-Reacting Substance of Anaphylaxis in the Late Bronchial Response After Antigen Challenge in Allergic Sheep", *Am. Rev. Respir. Dis.,* Vol. 130 (1984), pp. 748–754). Activity in cough is determined by measuring the number and latency of the cough response to respiratory challenges such as inhaled citric acid. (See, e.g., Callaway, J. & R. King, "Effects of Inhaled Alpha-2-Adrenoceptor and $GABA_B$ Receptor Agonists on Citric Acid-induced Cough and Tidal Volume Changes in Guinea Pigs", *Eur. J. Pharmacol.,* Vol. 220 (1992), pp. 187–195).

The compounds of the subject invention are synthesized using the following general procedure:

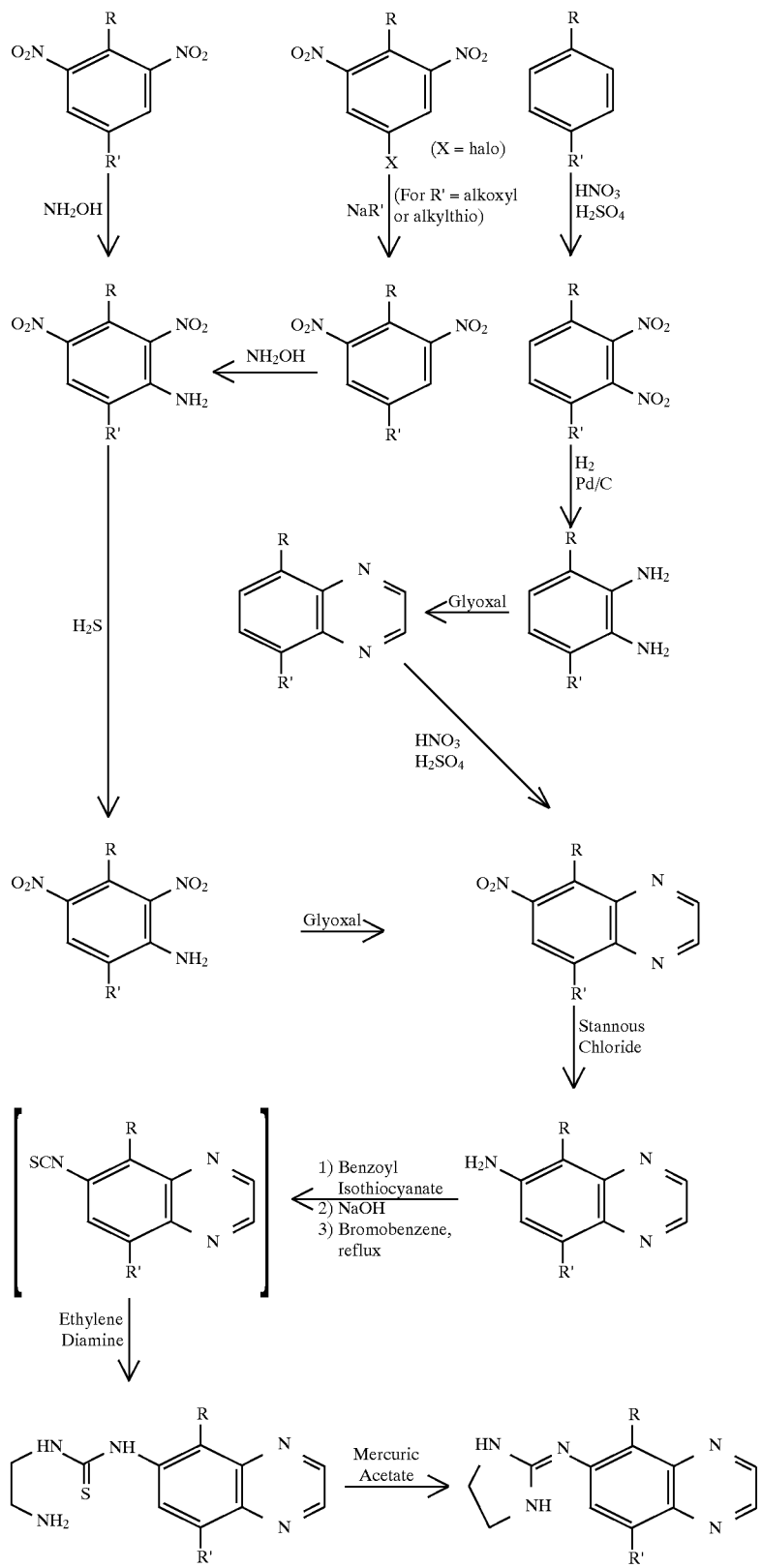
In the above scheme, where R' is alkoxy or alkylthio, the corresponding hydroxy or thiol compounds are derived from the final compounds by using a standard dealkylating procedure (Bhatt, et al., "Cleavage of Ethers", *Synthesis*, 1983, pp. 249–281).

The following non-limiting example provides details for the synthesis of 6-(2-imidazolinylamino)quinoxaline compounds useful in the subject invention.

EXAMPLE 1

Synthesis of 6-(2-imidazolinylamino)-5-methylquinoxaline:

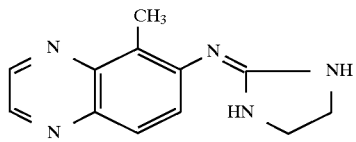

2,3-Diamino-6-nitrotoluene

To a solution of 3-methyl-2,4-dinitroaniline (30 g, prepared by the procedure of A. J. Boulton, P. B. Ghosh, A. R. Katritzky, *J. Chem Soc.* (B), 1011 (1966)) in boiling ethanol (750 mL) is added dropwise over 90 minutes a solution of sodium sulfide nonahydrate (109.6 g) in water (750 mL). At the end of the addition, the mixture is refluxed for 30 minutes then poured in ice (2000g) and allowed to stand until all the ice has melted. The mixture is then extracted with methylene chloride and the organic layer is dried over magnesium sulfate and rotary evaporated. The residue is purified by flash chromatography on silica gel, eluting with methylene chloride to afford 2,3-diamino-6-nitrotoluene as an orange solid.

5-Methyl6-nitroquinoxaline

To an 85° C. mixture of water (150 mL) and 2,3-diamino-6-nitrotoluene (4.2 g) is added glyoxal sodium bisulfite complex (8.6 g). After two hours stirring, the mixture is cooled to room temperature, treated with solid sodium hydroxide until a pH of 12–13 is reached and extracted with a 9/1 mixture of chloroform/methanol (4×500 mL). The combined organic layers are dried over potassium carbonate, filtered, and rotary evaporated to a residue which is vacuum sublimed at 120° C. to give 5-methyl-6-nitroquinoxaline.

6-Amino-5-methylquinoxaline

A mixture of 5-methyl-6-nitroquinoxaline (1.4 g), ethanol (100 mL) and stannous chloride dihydrate (7.2 g) is heated at reflux for three hours, cooled to below room temperature in an ice bath and treated with 1.0 N NaOH solution (120 mL). The mixture is then extracted with chloroform (2×1000 mL). The combined extracts are dried over potassium carbonate, filtered, and rotary evaporated to give 6-amino-5-methylquinoxaline.

6-(N'-Aminoethylthioureido)-5-methylquinoxaline

To a refluxing solution of benzoyl isothiocyanate (1.6 g) in dry acetone (20 mL) is added dropwise a solution of 6-amino-5-methylquinoxaline (1.2 g) in dry acetone (50 mL) over 30 minutes. The mixture is refluxed an additional two hours, cooled to room temperature, and rotary evaporated to a residue. This material is suspended in 10% NaOH solution (50 mL) forming a mixture which is heated at 90° C. for 30 minutes, then cooled to room temperature and adjusted to pH=8 by adding concentrated HCI. The mixture is then cooled in an ice bath and suction filtered. The collected solid thiourea intermediate is dried on a vacuum line (16 h, 0.5 torr), suspended in bromobenzene (50 mL) and heated at reflux for six hours to effect conversion to the isothiocyanate intermediate which is not isolated. The solution is cooled, then added dropwise to a solution of ethylene diamine (5.0 mL) in toluene (10 mL). The resulting mixture is stirred for 16 hours and filtered. The solids are washed with toluene (20 mL) and dried under vacuum to yield 6-(N'-aminoethylthioureido)-5-methylquinoxaline.

6-(2-Imidazolinylamino)-5-methylquinoxaline

A solution of 6-(N'-aminoethylthioureido)-5-methylquinoxaline (0.95 g) and mercuric acetate (1.22 g) in methanol (100 mL) is stirred at room temperature for 3 hours, filtered through a pad of Celite which is subsequently rinsed with methanol (2×300 mL). The combined methanol layers are rotary evaporated to a residue which is crystallized from benzene to yield 6-(2-imidazolinylamino)-5-methylquinoxaline. The mother liquor yields a second crop upon partial evaporation and crystallization.

The subject invention involves the use of compositions which comprise a safe and effective amount of a subject compound, or a pharmaceutically-acceptable salt thereof, and a pharmaceutically-acceptable carrier. As used herein, "safe and effective amount" means an amount of the subject compound sufficient to significantly induce a positive modification in the condition to be treated, but low enough to avoid serious side effects (at a reasonable benefit/risk ratio), within the scope of sound medical judgment. A safe and effective amount of the subject compound will vary with the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.0001% to about 99% by weight of the subject compound, more preferably from about 0.01% to about 90%; also preferably from about 10% to about 50%, also preferably from about 5% to about 10%, also preferably from about 1% to about 5%, and also preferably from about 0.1% to about 1%.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

The preferred mode of administering the subject compounds is perorally. The preferred unit dosage form is therefore tablets, capsules, lozenges, chewable tablets, and the like. Such unit dosage forms comprise a safe and effective amount of the subject compound, which is preferably from about 0.01 mg to about 200 mg, more preferably from about 0.1 mg to about 50 mg, more preferably still from about 0.5 mg to about 25 mg, also preferably from about 1 mg to about 10 mg. The pharmaceutically-acceptable carrier suitable for the preparation of unit dosage forms for peroral administration are well known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.001% to about 5% of the subject compound, more preferably from about 0.01% to about 0.5%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A preferred mode of administering the subject compounds is topically to the site where activity is desired: intranasal doses for nasal decongestion, inhalants for asthma, eye drops, gels and creams for ocular disorders, and peroral doses for gastrointestinal disorders.

Preferred compositions of the subject invention include aqueous solutions comprising a safe and effective amount of a subject compound intended for topical intranasal administration. Such compositions preferably comprise from about 0.001% to about 5% of a subject compound, more preferably from about 0.01% to about 0.5%. Such compositions also typically include safe and effective amounts of preservatives, such as benzalkonium chloride and thimerosal; buffers such as phosphate and acetate; tonicity agents such as sodium chloride; antioxidants such as ascorbic acid; aromatic agents; and acids and bases to adjust the pH of these aqueous compositions as needed.

Preferred compositions of the subject invention include aqueous solutions, suspensions, and dry powders comprising a safe and effective amount of a subject compound intended for atomization and topical inhalation administration. Such compositions preferably comprise from about 0.1% to about 50% of a subject compound, more preferably from about 1% to about 20%. Such compositions are typically contained in a container with attached atomizing means. Such compositions also typically include propellants such as chlorofluorocarbons 12/11 and 12/114; solvents such as water, glycerol and ethanol; stabilizers such as ascorbic acid, sodium metabisulfite; preservatives such as cetylpyridinium chloride and benzalkonium chloride; tonicity adjustors such as sodium chloride; and flavoring agents such as sodium saccharin.

Preferred compositions of the subject invention include aqueous solutions comprising a safe and effective amount of a subject compound intended for topical intraocular administration. Such compositions preferably comprise from about 0.0001% to about 5% of a subject compound, more preferably from about 0.01% to about 0.5%. Such compositions also typically include one or more of preservatives, such as benzalkonium chloride, thimerosal, phenylmercuric acetate; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases may be used to adjust the pH of these formulations as needed.

Preferred compositions of the subject invention include solids, such as tablets and capsules, and liquids, such as solutions, suspensions and emulsions (preferably in soft gelatin capsules), comprising a safe and effective amount of a subject compound intended for topical administration to the gastrointestinal tract by peroral administration. Such compositions preferably comprise from about 0.01 mg to about 100 mg per dose, more preferably from about 0.1 mg to about 5 mg per dose. Such compositions can be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Compositions of the subject invention may optionally include other drug actives. Non-limiting examples of drug actives which may be incorporated in the subject compositions, and typical dosage amounts of them, include: respiratory drug actives: classical antihistamines, e.g., chlorpheniramine from about 1 mg to about 4 mg per dose, and diphenhydramine from about 10 mg to about 50 mg per dose; nonsedating antihistamines, e.g., terfenadine from about 30 mg to about 60 mg per dose, loratadine from about 5 mg per dose to about 10 mg per dose, and cetirizine from about 5 mg per dose to about 10 mg per dose; expectorants, e.g., guaifenesin from about 100 mg to about 200 mg per dose; antitussives, e.g., dextromethorphan from about 5 mg to about 30 mg per dose; and analgesics, e.g., ibuprofen from about 100 mg to about 800 mg per dose, and acetaminophen from about 80 mg to about 1000 mg per dose; ocular drug actives: acetylcholinesterase inhibitors, e.g., echothiophate from about 0.03% to about 0.25% in topical solution; and gastrointestinal actives: antidiarrheals, e.g., loperamide from about 0.1 mg to about 1.0 mg per dose, and bismuth subsalicylate from about 25 mg to about 300 mg per dose.

The subject invention involves methods for preventing or treating nasal congestion by administering a safe and effective amount of a subject compound to a human or lower animal experiencing or at risk of experiencing nasal congestion. Such nasal congestion may be associated with human diseases or disorders which include, but are not limited to, seasonal allergic rhinitis, acute upper respiratory viral infections, sinusitis, perennial rhinitis, and vasomotor rhinitis. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. Peroral administration of such doses is preferred. The frequency of administration of a subject compound according to the subject invention is preferably from about once to about six times daily, more preferably from about 2 times to about 4 times daily. Such doses and frequencies are also preferred for treating other respiratory conditions, such as otitis media, cough, COPD and asthma.

Another aspect of the subject invention involves methods for preventing or treating glaucoma by administering a safe and effective amount of a subject compound to a human or lower animal experiencing or at risk of experiencing glaucoma. Each administration of a dose of the subject compound preferably administers a dose within the range of from about 0.01 $\mu$g/kg to about 10 mg/kg of a compound, more preferably from about 0.001 mg/kg to about 1 mg/kg, more preferably still from about 0.01 mg/kg to about 0.1 mg/kg. Intraocular administration of such doses is preferred. The frequency of administration of a subject compound according to the subject invention is preferably from about once to about six times daily, more preferably from about 2 times to about 4 times daily.

Another aspect of the subject invention involves methods for preventing or treating functional bowel disorders, such as diarrhea, by administering a safe and effective amount of a subject compound to a human or lower animal experiencing or at risk of experiencing diarrhea. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. Peroral administration of such doses is preferred. The frequency of administration of a subject compound according to the subject invention is preferably from about once to about six times daily, more preferably from about 2 times to about 4 times daily.

The following non-limiting examples illustrate the compounds, compositions and methods of use of the subject invention.

EXAMPLE 2

Example 2
Oral Tablet Composition

| Ingredient | Amount per tablet (mg) |
|---|---|
| Subject Compound 1 | 20.0 |
| Microcrystalline cellulose (Avicel PH 102 ®) | 80.0 |
| Dicalcium phosphate | 96.0 |
| Pyrogenic silica (Cab-O-Sil ®) | 1.0 |
| Magnesium stearate | 3.0 |
| Total = | 200.0 |

One tablet is swallowed by a patient with nasal congestion. The congestion is substantially diminished.

Example 3
Chewable Tablet Composition

| Ingredient | Amount per tablet (mg) |
|---|---|
| Subject Compound 1 | 15.0 |
| Mannitol | 255.6 |
| Microcylstalline cellulose (Avicel PH 101 ®) | 100.8 |
| Dextrinized sucrose (Di-Pac ®) | 199.5 |
| Imitation orange flavor | 4.2 |
| Sodium saccharin | 1.2 |
| Stearic acid | 15.0 |
| Magnesium stearate | 3.0 |
| FD&C Yellow #6 dye | 3.0 |
| Pyrogenic silica (Cab-O-Sil ®) | 2.7 |
| Total = | 600.0 |

One tablet is chewed and swallowed by a patient with nasal congestion. The congestion is substantially reduced.

Example 4
Sublingual Tablet Composition

| Ingredient | Amount per tablet (mg) |
|---|---|
| Subject Compound 1 | 2.00 |
| Mannitol | 2.00 |
| Microcrystalline cellulose (Avicel PH 101 ®) | 29.00 |
| Mint flavorants | 0.25 |
| Sodium saccharin | 0.08 |
| Total = | 33.33 |

One tablet is place under the tongue of a patient with nasal congestion and allowed to dissolve. The congestion is rapidly and substially diminished.

Example 5
Intranasal Solution Composition

| Ingredient | Composition (% w/v) |
|---|---|
| Subject Compound 1 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

One-tenth of a mL of the composition is sprayed from a pump actuator into each nostril of a patient with nasal congestion. The congestion is substantially diminished.

Example 6
Intranasal Gel Composition

| Ingredient | Composition (% w/v) |
|---|---|
| Subject Compound 1 | 0.10 |
| Benzalkonium chloride | 0.02 |
| Thimerosal | 0.002 |
| Hydroxypropyl methylcellulose (Metolose 65SH4000 ®) | 1.00 |
| Aromatics | 0.06 |
| Sodium chloride (0.65%) | q.s. |
| Total = | 100.00 |

One-fifth of a mL of the composition is applied as drops from a dropper into each nostril of a patient with nasal congestion. The congestion is substantially reduced.

Example 7
Inhalation Aerosol Composition

| Ingredient | Composition (% w/v) |
|---|---|
| Subject Compound 1 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

Two-puffs of the aerosol composition is inhaled from a metered-dose inhaler by a patient with asthma. The asthmatic condition is effectively relieved.

Example 8
Topical Ophthalmic Composition

| Ingredient | Composition (% w/v) |
|---|---|
| Subject Compound 1 | 0.10 |
| Benzalkonium chloride | 0.01 |
| EDTA | 0.05 |
| Hydroxyethylcellulose (Natrosol M ®) | 0.50 |
| Sodium metabisulfite | 0.10 |
| Sodium chloride (0.9%) | q.s. |
| Total = | 100.0 |

One-tenth of a mL of the composition is administered directly into each eye of a patient with glaucoma. The intraocular pressure is substantially reduced.

Example 9
Oral Liquid Composition

| Ingredient | Amount/15 mL Dose |
|---|---|
| Subject Compound 1 | 15 mg |
| Chlorpheniramine maleate | 4 mg |
| Propylene glycol | 1.8 g |
| Ethanol (95%) | 1.5 mL |
| Methanol | 12.5 mg |
| Eucalyptus oil | 7.55 mg |
| Flavorants | 0.05 mL |
| Sucrose | 0.76 g |
| Carboxymethylcellulose (CMC) | 7.5 mg |
| Microcrystalline cellulose and Sodium CMC (Avicel RC 591 ®) | 187.5 mg |
| Polysorbate 80 | 3.0 mg |
| Glycerin | 300 mg |
| Sorbitol | 300 mg |
| FD&C Red #40 dye | 3 mg |
| Sodium saccharin | 22.5 mg |
| Sodium phosphate monobasic | 44 mg |
| Sodium citrate monohydrate | 28 mg |
| Purified Water | q.s. |
| Total = | 15 mL |

One 15 mL dose of the liquid composition is swallowed by a patient with nasal congestion and runny nose due to allergic rhinitis. The congestion and runny nose are effectively reduced.

Example 10
Oral Liquid Composition

| Ingredient | Amount/15 mL Dose |
|---|---|
| Subject Compound 1 | 30 mg |
| Sucrose | 8.16 g |
| Glycerin | 300 mg |
| Sorbitol | 300 mg |
| Methylparaben | 19.5 mg |
| Propylparaben | 4.5 mg |
| Methanol | 22.5 mg |
| Eucalyptus oil | 7.5 mg |
| Flavorants | 0.07 mL |
| FD&C Red #40 dye | 3.0 mg |
| Sodium saccharin | 30 mg |
| Purified water | q.s. |
| Total = | 15 mL |

One 15 mL dose of the alcohol-free liquid medication is swallowed by a patient with nasal congestion. The congestion is substantially diminished.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A method of treating nasal congestion comprising administration, to a human or lower animal in need of such treatment, of a safe and effective amount of a compound having the following structure:

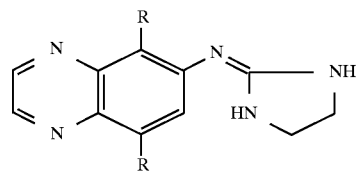

wherein:
(a) R is unsubstituted alkanyl or alkenyl having from 1 to about 3 carbon atoms; and
(b) R' is selected from the group consisting of hydrogen; unsubstituted alkanyl or alkenyl having from 1 to about 3 carbon atoms; unsubstituted alkylthio or alkoxy having from 1 to about 3 carbon atoms; hydroxy; thiol; and halo.

2. The method of claim 1 wherein the compound is administered perorally to the human or lower animal.

3. The method of claim 2 wherein any alkyl portion of R' is methyl.

4. The method of claim 2 wherein R is alkanyl.

5. The method of claim 4 wherein R' is hydrogen or alkanyl.

6. The method of claim 4 wherein R' is selected from the group consisting of hydrogen, methyl, ethyl, methoxy, chloro and bromo.

7. The method of claim 3 wherein R is methyl.

8. The method of claim 6 wherein R is methyl.

9. The method of claim 4 wherein R' is hydrogen.

10. The method of claim 8 wherein R' is hydrogen.

* * * * *